(12) United States Patent
Baribeau

(10) Patent No.: US 10,705,020 B2
(45) Date of Patent: Jul. 7, 2020

(54) METHOD AND APPARATUS FOR OPTICAL DETECTION OF BIO-CONTAMINANTS WITHIN A LUMEN

(71) Applicants: STERIS Inc., Temecula, CA (US);
National Optics Institute, Quebec City (CA)

(72) Inventor: Francois Baribeau, Quebec (CA)

(73) Assignees: STERIS Inc., Temecula, CA (US);
National Optics Institute, Quebec City (CA)

(*) Notice: Subject to any disclaimer, the term of this patent is extended or adjusted under 35 U.S.C. 154(b) by 250 days.

(21) Appl. No.: 15/802,505

(22) Filed: Nov. 3, 2017

(65) Prior Publication Data
US 2018/0067051 A1    Mar. 8, 2018

Related U.S. Application Data

(63) Continuation-in-part of application No. 15/142,309, filed on Apr. 29, 2016, now Pat. No. 10,036,705, which is a continuation of application No. 13/777,053, filed on Feb. 26, 2013, now Pat. No. 9,354,182.

(51) Int. Cl.
| | | |
|---|---|---|
| *G01N 21/64* | (2006.01) | |
| *A61L 2/28* | (2006.01) | |
| *G01N 21/94* | (2006.01) | |
| *G01N 21/954* | (2006.01) | |

(52) U.S. Cl.
CPC .......... *G01N 21/6428* (2013.01); *A61L 2/28* (2013.01); *G01N 21/6486* (2013.01); *G01N 21/94* (2013.01); *G01N 21/954* (2013.01); *A61L 2202/24* (2013.01); *G01N 2021/6417* (2013.01); *G01N 2021/6439* (2013.01); *G01N 2201/068* (2013.01); *G01N 2201/0697* (2013.01);
(Continued)

(58) Field of Classification Search
None
See application file for complete search history.

(56) References Cited

U.S. PATENT DOCUMENTS

| | | | |
|---|---|---|---|
| 2,600,221 A | 6/1952 | Domingo | 250/71 |
| 4,932,227 A | 6/1990 | Hogrefe | 68/17 R |

(Continued)

FOREIGN PATENT DOCUMENTS

| | | | |
|---|---|---|---|
| EP | 0697590 A1 | 2/1996 | |
| WO | WO 2012/022945 | 2/2012 | G01N 33/50 |
| WO | WO 2012/022963 | 2/2012 | G01N 21/64 |

OTHER PUBLICATIONS

PR Newswire, United Business Media, "Block Engineering Announces Collaborative Agreement with Pfizer for Next Generation Cleaning Verification Technology," article obtained from website www.prnewswire.com/news-releases/block-engineering-announces-collaborative-agreement-with-pfizer-for-next-generation-cleaning-verification-technology-187438201.html, last accessed Mar. 18, 2013.
(Continued)

*Primary Examiner* — Xiaoyun R Xu
(74) *Attorney, Agent, or Firm* — Kusner & Jaffe

(57) ABSTRACT

A method for optical detection of residual soil in lumens of lumened or cannulated devices such as surgical endoscopes, after undergoing a decontamination process (e.g., a washing or rinsing operation). A soil detection system provides an indication of the presence of residual soil within a lumen by detecting luminescent radiation emanating from the soil on the interior of the lumen in response to excitation light.

15 Claims, 14 Drawing Sheets

(52) U.S. Cl.
CPC .............. *G01N 2201/06113* (2013.01); *G01N 2201/10* (2013.01); *G01N 2201/105* (2013.01)

(56) References Cited

U.S. PATENT DOCUMENTS

| | | | |
|---|---|---|---|
| 4,938,224 A | 7/1990 | Rysavy | 128/633 |
| 5,225,675 A | 7/1993 | O'Donnell | 250/302 |
| 5,396,178 A | 3/1995 | Rybarski | 324/439 |
| 5,747,794 A | 5/1998 | Malchesky | 250/227.23 |
| 5,749,385 A | 5/1998 | Rochette et al. | 134/199 |
| 5,759,289 A | 6/1998 | Caron et al. | 134/34 |
| 5,863,790 A | 1/1999 | Bolea | 435/287.4 |
| 5,900,067 A | 5/1999 | Jones | 134/1 |
| 5,906,802 A | 5/1999 | Langford | 422/300 |
| 5,923,432 A | 7/1999 | Kral | 356/432 |
| 5,928,948 A | 7/1999 | Malchesky | 436/2 |
| 6,021,344 A | 2/2000 | Lui | 351/159.3 |
| 6,394,111 B1 | 5/2002 | Jacobs et al. | 134/113 |
| 6,454,874 B1 | 9/2002 | Jacobs et al. | 134/18 |
| 6,494,964 B1 | 12/2002 | Jacobs et al. | 134/18 |
| 6,516,817 B2 | 2/2003 | Jacobs et al. | 134/113 |
| 6,516,818 B2 | 2/2003 | Jacobs et al. | 134/113 |
| 6,524,390 B1 | 2/2003 | Jones | 134/1 |
| 6,571,812 B1 | 6/2003 | Lavoie et al. | 134/191 |
| 6,653,146 B1 | 11/2003 | Ruvinsky et al. | 436/172 |
| 6,666,218 B2 | 12/2003 | Lavoie et al. | 134/25.2 |
| 6,683,735 B2 | 1/2004 | Stuckey | 359/831 |
| 6,737,645 B2 | 5/2004 | Foster et al. | 250/302 |
| 7,439,217 B2 | 10/2008 | Boutique et al. | 510/287 |
| 8,140,141 B2 | 3/2012 | McGreevy et al. | 600/317 |
| 2003/0135092 A1 | 7/2003 | Cline et al. | 600/160 |
| 2003/0185966 A1 | 10/2003 | Kim et al. | 428/8 |
| 2003/0205862 A1 | 11/2003 | Kapoor et al. | 250/458.1 |
| 2004/0010192 A1 | 1/2004 | Benaron | 600/431 |
| 2006/0153508 A1 | 7/2006 | Bowker et al. | |
| 2007/0109536 A1 | 5/2007 | Weiss et al. | 356/318 |
| 2008/0061236 A1 | 3/2008 | Meredith et al. | 250/338.1 |
| 2009/0109408 A1 | 4/2009 | Hsiung | 353/84 |
| 2010/0252437 A1 | 10/2010 | Amirkhanian et al. | |
| 2012/0021406 A1 | 1/2012 | Franciskovich et al. | 435/5 |
| 2012/0033220 A1 | 2/2012 | Kotidis et al. | 356/445 |
| 2012/0315627 A1 | 12/2012 | Aojula et al. | 435/5 |
| 2014/0242717 A1 | 8/2014 | Rochette et al. | 436/172 |
| 2016/0349179 A1 | 12/2016 | Rochette et al. | |
| 2018/0067051 A1 | 3/2018 | Baribeau | |

OTHER PUBLICATIONS

Website pring out of "Proreveal Fluorescence Protein Detection Test Overview," www.synopticshealth.com/overview/, print out date Oct. 28, 2013.

Website print out of "Synoptics Health Proreveal Technical FAQs," www.synopticshealth.com/faqs, print out date Oct. 28, 2013.

Website print out of "Proreveal Fluorescence Protein Detection Test Technical Data Sheet," www.synopticshealth.com/assets/doc/Proreveal-tech-sheet-final.pdf, print out date Oct. 28, 2013.

Novak et al., "An integrated fluorescence detection system for lab-on-a-chip applications," 2007, Lap on a Chip, vol. 7, pp. 27-29.

Fujiki et al., Quantification of Green Fluorescent Protein by In Vivo Imaging, PCR, and Flow Cytometry: Comparison of Transgenic Strains and Relevance for Fetal Cell Microchimerism, 2008, Cytometry Par A, vol. 74A, pp. 111-118.

Young, Martha, "Lumens and endoscopes: Meeting cleaning basics," *Sterilization & Infection Control*, OR Manager, Inc., Aug. 2012, vol. 28, No. 8, pp. 1-5.

Stephenson, Kevin, "The Value of Lumen Inspection See What You Have Been Missing," Vendor Vantage, Communiqué, May/Jun. 2015, pp. 76-78.

Smith, Matt, "Instructions for Use: Flexible Inspection Scope Camera," Healthmark Industries Company, Inc., Health Care Products, Oct. 10, 2014.

Drosnock, Mary Ann, "Use of the Flexible Inspection Scope (FIS) for Inspection of Flexible Endoscopes and Other Medical Devices," Healthmark Industries Company, Inc., Health Care Products, Sep. 2016.

METHOD AND APPARATUS FOR OPTICAL DETECTION OF BIO-CONTAMINANTS WITHIN A LUMEN

RELATED APPLICATIONS

The present application is a continuation-in-part of U.S. application Ser. No. 15/142,309, filed Apr. 29, 2016 (now U.S. Pat. No. 10,036,705, issued Jul. 31, 2018), which is a continuation of U.S. application Ser. No. 13/777,053, filed Feb. 26, 2013 now U.S. Pat. No. 9,354,182, issued May 31, 2016), said patent applications fully incorporated herein by reference.

FIELD OF THE INVENTION

The present invention relates generally to the cleaning and decontaminating arts, and more particularly to a method and apparatus for inspection of lumened or cannulated devices after undergoing a decontamination process. In particular, the present invention relates to a method and apparatus for optical detection of biological contaminants within lumens of lumened or cannulated devices such as endoscopes.

BACKGROUND OF THE INVENTION

Medical washers are conventionally known and are used to clean articles (e.g., medical devices, such as medical instruments and equipment) that have been exposed to bio-contaminants. Such washers typically clean the articles to remove bio-contaminants by directing jets or streams of fluid at the articles from spray heads or nozzles located within the washer. A typical cleaning operation may include a preliminary rinse cycle, a pre-wash cycle, a wash cycle, a post-wash rinse cycle, a thermal rinse cycle and a drying cycle. During the rinse and wash cycles the articles are exposed to one or more chemical cleaning and rinsing solutions.

It is not unusual for a cleaning operation to be followed by a visual inspection conducted by a human to insure that there are no residual bio-contaminants (hereinafter referred to as "soil") on the articles. The soil may include organic residues including, but not limited to, blood, fat, mucous, lipids, carbohydrates, bone, hair, protein, and food product. Some articles have unique shapes, corners or crevices that make removal of the bio-contaminants therefrom difficult. Human visual inspection helps ensure that post-wash articles with soil thereon are not allowed to proceed to further processing (e.g., sterilization) without first removing any remaining bio-contaminants.

As will be appreciated, a human visual inspection is both time-consuming and costly. Moreover, it is difficult to detect minute amounts of soil by human visual inspection, and such visual inspection is subject to human error (for example, person-to-person variations and individual biases). Furthermore, it is observed that human visual inspection is a binary qualitative process, not quantitative.

Medical washing is only one example of a field in which there is a need for decontamination and inspection procedures. Similar decontamination and inspection procedures are performed in other, different fields of endeavor, including fields in which industrial processing equipment is exposed to organic residues. Such fields include the agrifood sector, such as dairy, brewery, and other food processing facilities.

Some prior art methods for optical detection of soil use a fluorescent dye or agent to detect the presence of soil on an article. In such systems, the fluorescent agent is applied to the article, for example, by exposing the article to a solution that includes the fluorescent agent. The fluorescent agent binds to organic residues (e.g., proteins), and thus affixes to the soil to label the bio-contaminant. Where there is no soil on the article, the fluorescent agent does not become affixed thereto, and thus can be washed off. To provide optical detection of the soil according to certain prior art methods, the article can be exposed to "black light" (i.e., electromagnetic radiation in the ultraviolet range having wavelengths around 315-400 nm), which is absorbed by the fluorescent agent. Absorbance of this ultraviolet (UV) light causes the fluorescent agent to emit visible light (i.e., to be fluorescent), thereby identifying the presence of soil to a human inspector. A typical human eye is responsive to light in the wavelength range of 390-750 nm. A fluorophore such as fluorescein has an excitation under light having a wavelength of about 488-490 nm, upon which the fluorescein emits light (i.e., fluoresces) at a wavelength of about 513 nm.

This prior art method does not allow personnel to carry out their task of reprocessing of articles in desirable ambient light conditions, and thus makes it difficult for personnel to disassemble, reassemble, and inspect articles for cleanliness. Recommended illuminance levels for such work environments can range from 200 lux to 2000 lux, and more typically range from 1400 lux to 2000 lux.

It is becoming increasingly common to utilize cannulated or lumened devices within the surgical operating room. It is understood in the art that a "lumen" is a cavity within the interior space of a tubular passageway or structure. There are a wide variety of lumened instruments in use today. The cost of instruments such as endoscopes is often very high, and so thorough reprocessing is becoming increasingly desirable.

One significant challenge is the detection of any residual soil remaining inside the inner portion of a lumen after manual cleaning of the interior of the lumen by use of a brush or a swab. Prior art approaches to confirming cleanliness are labor-intensive and thus very expensive while not very precise. Visual inspection is only qualitative and the detection and/or integrity of cleanliness validation is dependent on human error.

The present invention provides a method and apparatus for optical detection of soil in a lumen of a medical instrument, such as an endoscope.

The present invention also provides a method and apparatus for optical inspection of other types of lumened and cannulated structures, such as small pipes and tubes included in industrial applications such as agrifood (dairy, brewery, and other food processing facilities).

SUMMARY OF THE INVENTION

According to a first aspect of the present invention, there is provided a soil detection system for detecting presence of soil on an article, the soil detection system comprising: (a) a scanning unit including: a light source for producing light to be incident on the article; a detector for detecting electromagnetic radiation emanating from said article and generating light data corresponding thereto, said electromagnetic radiation including ambient light reflected by the article and light emitted by an excited luminescent agent that is bound to the soil, and a light filter for filtering light of predetermined frequencies; and (b) a control unit for receiving the light data generated by the detector to determine the presence of soil on the article.

According to another aspect of the present invention, there is provided a method for detecting presence of soil on an article, said method comprising: introducing a luminescent agent to a detergent during a wash cycle of a washing apparatus, wherein the luminescent agent is bound to soil present on the article; rinsing the article to remove unbound luminescent agent; exposing the article to laser light; detecting light emanating from said article and generating light data corresponding thereto, said light emanating from said article including ambient light reflected by the article and light emitted by exciting the luminescent agent bound to the soil; filtering the light emanating from said article at predetermined frequencies; and determining the presence of soil on the article based upon the filtered light received by a light detector.

According to yet another aspect of the present invention, there is provided a soil detection system for detecting presence of soil inside a cannulated structure such as a lumen, the soil detection system comprising: (a) a probe for insertion into an interior of the lumen to detect a fluorescent agent bound to residual soil present on the interior of the lumen, the fluorescent agent emitting fluorescent light at a fluorescence wavelength indicative of soil in response to excitation light at an excitation wavelength; (b) a light source for producing the excitation light at the excitation wavelength, transmitted through a distal end of the probe into the interior of the lumen; (c) a light filter for filtering light emanating from the interior of the lumen, said light emanating from said interior including the excitation light reflected by the interior at the excitation wavelength and the fluorescent light at the fluorescence wavelength emitted by exciting the fluorescent agent bound to the soil with the excitation light, said light filter configured to pass the fluorescent light indicative of soil; (d) a photodetector for detecting the filtered fluorescent light emanating from said interior and generating a light signal corresponding thereto; and (e) a processing unit for receiving the light signal generated by the detector to determine a presence of soil on the interior based upon features detected at the fluorescence wavelength within the interior of the lumen.

According to still another aspect of the present invention, there is provided a method for detecting presence of soil within a lumen, said method comprising: introducing a fluorescent agent to a detergent during a wash cycle of a washing apparatus, wherein the fluorescent agent emits fluorescent light at a fluorescence wavelength, said fluorescent agent bound to soil present on an interior of the lumen; rinsing the lumen to remove unbound fluorescent agent; exposing the interior of the lumen to excitation light at an excitation wavelength; filtering the light emanating from the interior of the lumen, said light emanating from said interior including the excitation light reflected by the interior at the excitation wavelength and the fluorescent light at the fluorescence wavelength emitted by exciting the fluorescent agent bound to the soil with the excitation light, said filtering passes the fluorescent light indicative of soil; detecting the filtered fluorescent light emanating from the interior of said lumen; and determining the presence of soil on the interior based upon features detected at the fluorescence wavelength within the interior of the lumen.

An advantage of the present invention is the provision of a method and apparatus that uses optical excitation and luminescence (such as fluorescence) to detect the presence of soil on articles that have undergone a washing or rinsing process.

Still another advantage of the present invention is the provision of a method and apparatus that allows optical detection of soil on articles in the presence of ambient light.

Yet another advantage of the present invention is the provision of a method and apparatus that uses optical excitation and luminescence (such as fluorescence) to detect the presence of residual soil within a lumened or cannulated instrument that has undergone a decontamination process, such as washing or rinsing.

Another further advantage of the present invention is the provision of a method and apparatus that allows optical detection of soil within a lumen in the presence of ambient light.

These and other advantages will become apparent from the following description of the present invention, taken together with the accompanying drawings and the appended claims.

BRIEF DESCRIPTION OF THE DRAWINGS

The present invention may take physical form in certain parts and arrangement of parts, preferred embodiments of which will be described in detail in the specification and illustrated in the accompanying drawings which form a part hereof, and wherein.

DETAILED DESCRIPTION OF THE INVENTION

It should be appreciated that the term "medical devices" as used herein, includes, but is not limited to, such articles as surgical, dental, veterinary and mortuary instruments and equipment. The articles may be made of various materials, including, but not limited to, stainless steel.

Figure 1:
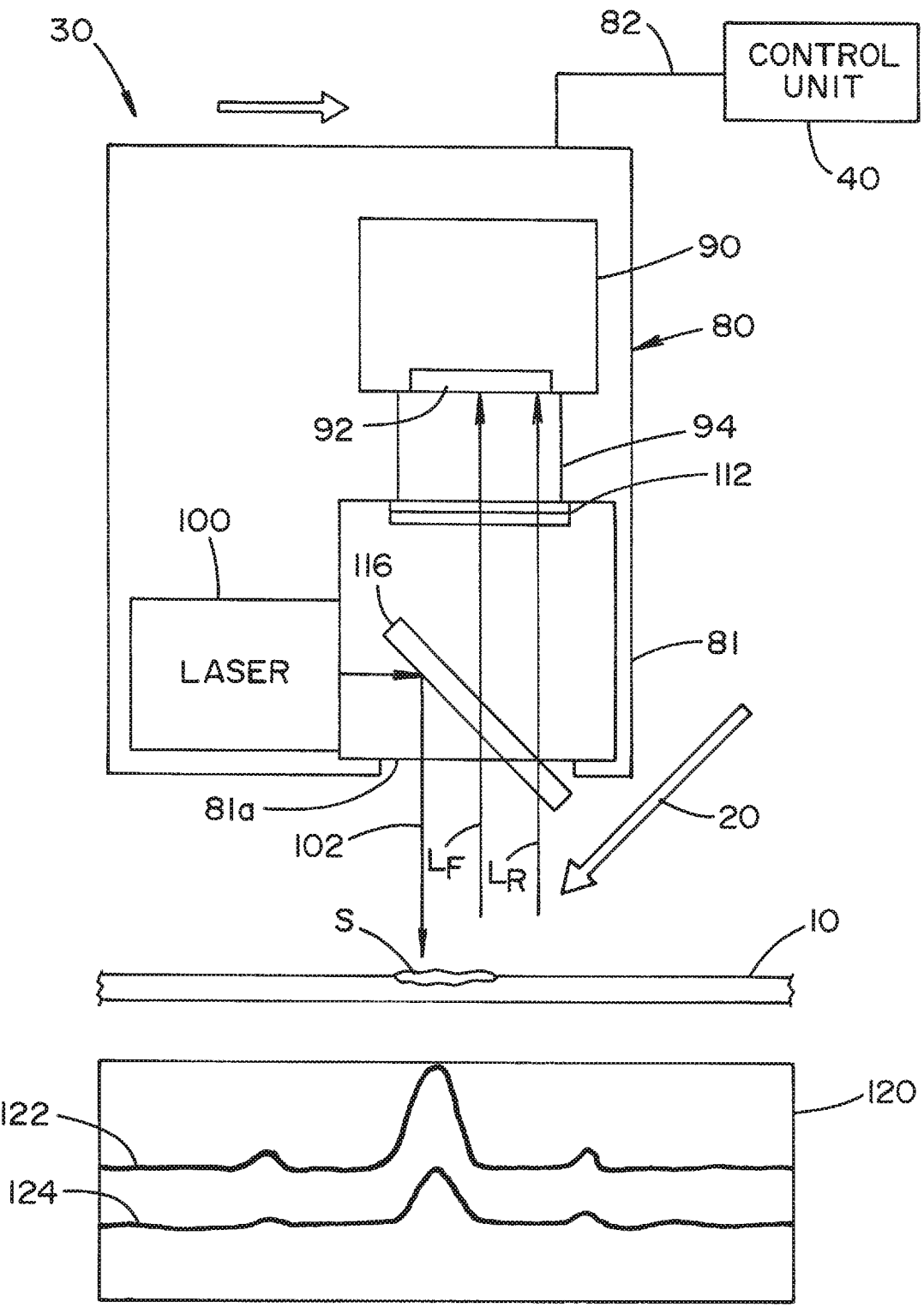
FIG. 1 is a schematic view of a soil detection system according to a first embodiment of the present invention.
Figure 3:
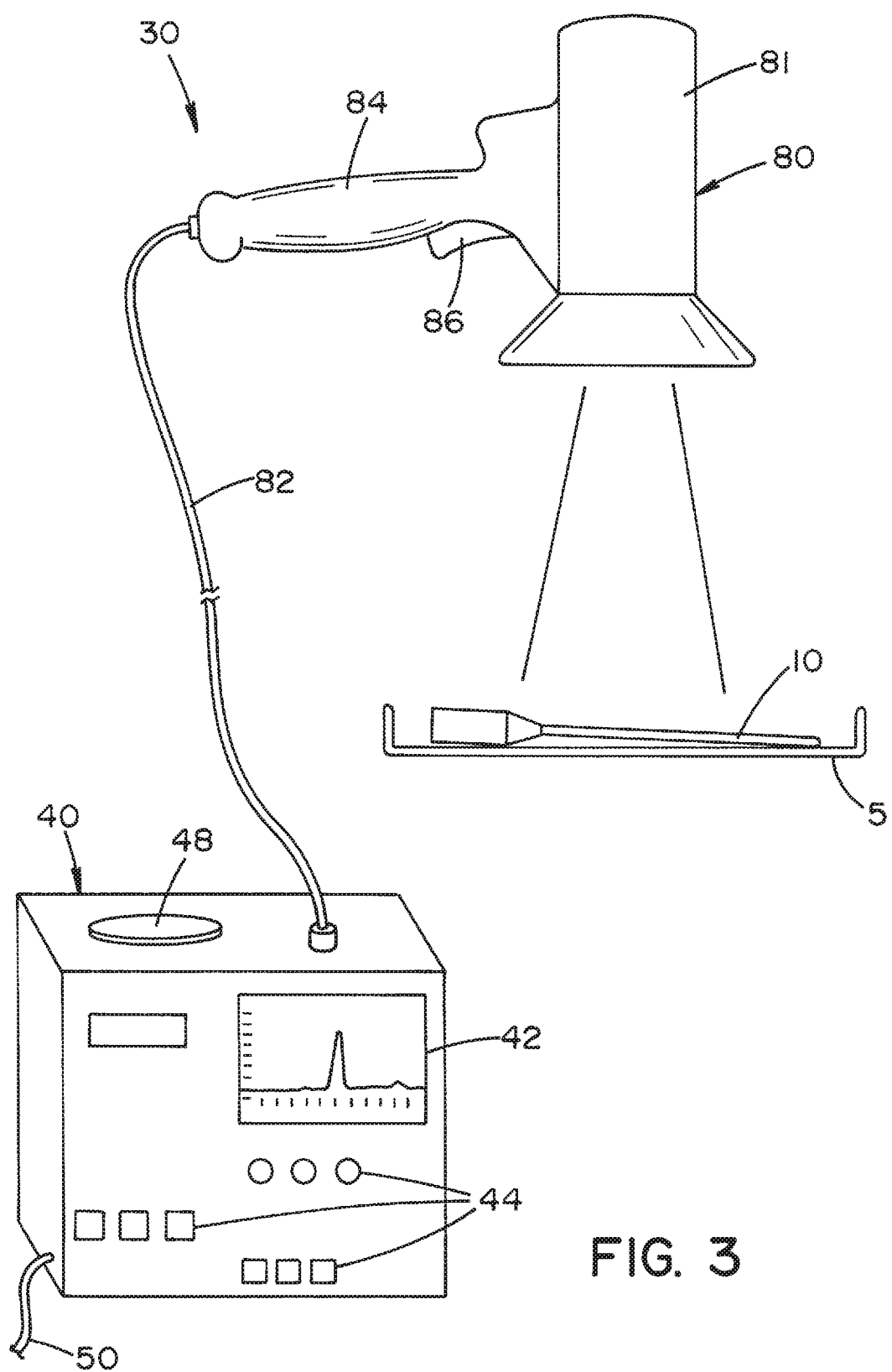
FIG. 3 is a detailed illustration of a soil detection system according to the first embodiment of the present invention.
Figure 4A:
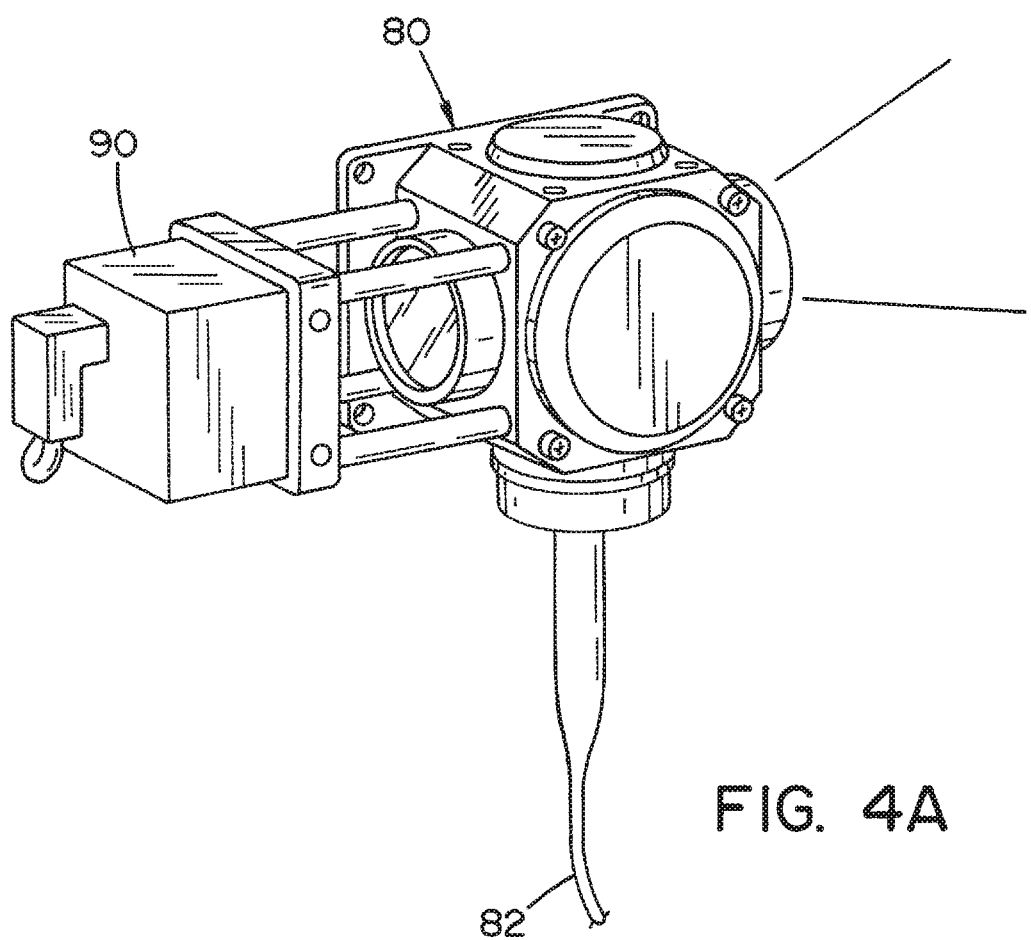
FIGS. 4A and 4B illustrate internal components of a scanning unit for the soil detection system.
Figure 4B:
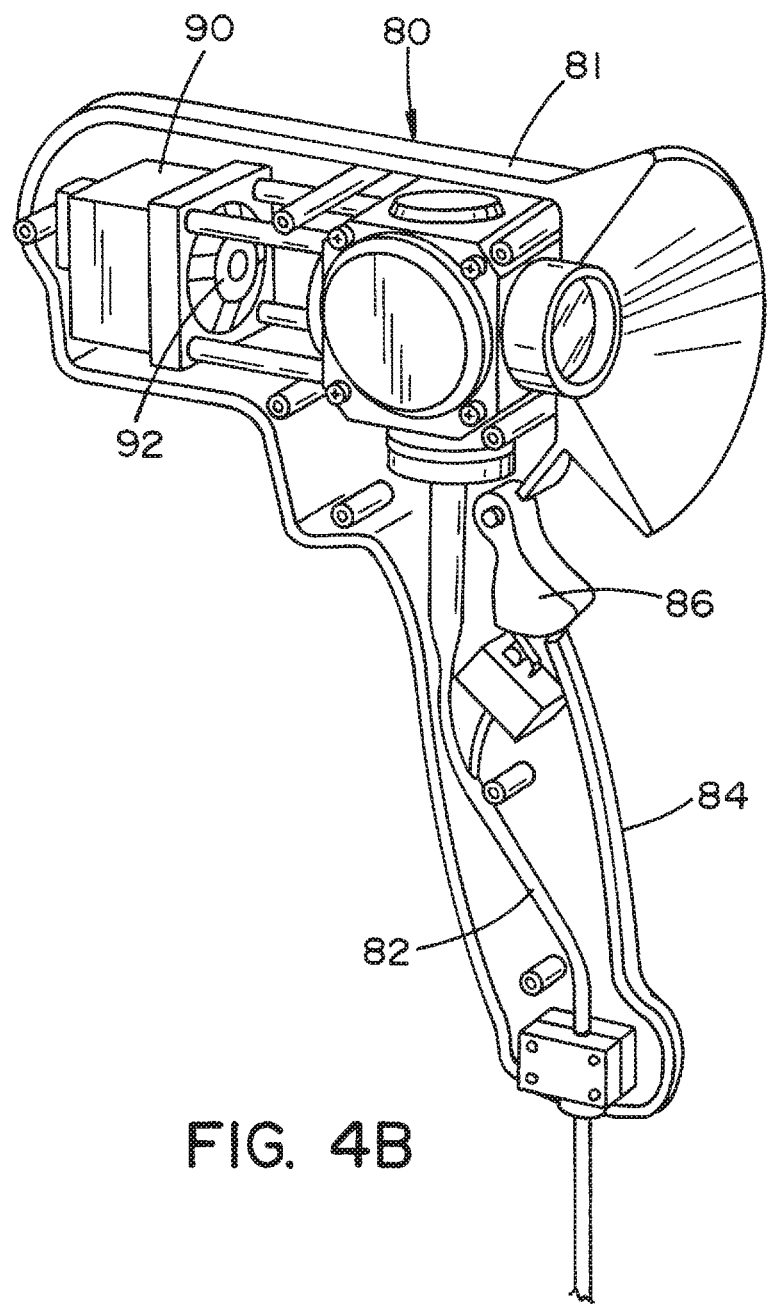

Referring now to FIGS. 1 and 3, there is shown a soil detection system 30 according to an embodiment of the present invention, generally comprised of a scanning unit 80 and a control unit 40. Scanning unit 80 includes a detector 90, a light source in the form of a laser 100 that produces a laser light 102, a light filter 112, and a dichroic beamsplitter 116 that are located within a housing 81. In the illustrated embodiment, scanning unit 80 is handheld by the user. It should be understood that the light source can alternatively be located external to scanning unit 80 and an optical fiber used to transmit light from the external light source to scanning unit 80.

In the illustrated embodiment, detector 90 takes the form of a conventional digital video/still camera that includes a CMOS (complementary metal-oxide semiconductor) or CCD (charge-coupled device) image sensor 92 and a lens 94. A CCD image sensor 92 represents pixels by p-doped MOSFET capacitors. These capacitors are biased above the threshold for inversion when image acquisition begins, allowing the conversion of incoming photons into electron charges at the semiconductor-oxide interface. Image sensor 92 is then used to read out these charges. Detector 90 is adapted to detect electromagnetic radiation emanating from said articles and generate corresponding information (i.e., light data) that is delivered to control unit 40. It should be understood that detector 90 may take the form of any suitable device able to detect electromagnetic radiation and produce an image, including, but not limited to, a CMOS sensor, a CCD, a photodiode, and a photodiode array. In the illustrated embodiment, image sensor 92 takes the form of a color image sensor, such as CCD or CMOS with RGB (Red-Green-Blue) pixel matrix, or a three-dimensional image sensor where color RGB planes are stacked on the same chip, such as 3-CCD or 3-CMOS. These image sensors provide access to each color channel individually for image processing.

In the illustrated embodiment, laser 100 is preferably a laser diode that predominantly emits light ("laser light") at a wavelength of about 488-490 nm (blue). As will be explained in further detail below, the laser light excites a fluorescent agent (e.g., a fluorophore such as fluorescein). Two- and three-dimensional images may be obtained since fluorescence takes place in all directions (i.e., the fluorescence signal is usually isotropic). Furthermore, the signal-to-noise ratio of the fluorescence signal is very high, providing a good sensitivity. In the illustrated embodiment, the fluorescent agent is fluorescein, which has a maximum excitation at light having a wavelength of about 488-490 nm. Once excited, the fluorescein emits light at a wavelength of about 513 nm. Since the emitted, fluorescent light is of a different frequency than the excitation light, the excitation light can be filtered out. The intensity of light emitted from a region having the fluorescent agent is correlated to the intensity of excitation energy and to the concentration of the fluorescent agent.

It should be understood that the light source of the present invention for producing light emitted by scanning unit 80 may take a number of different forms, including, but not limited to, any kind of device being able to emit a monochromatic or broadband electromagnetic field. Examples of such devices include lasers, solid-state lasers, laser diodes, argon ion lasers, micro wire lasers, diode solid-state lasers, vertical cavity surface emitting lasers, light emitting diodes (LED), organic light emitting diode (OLED), polymer light emitting diode (PLED), quantum dot based light sources, white light sources, halogen lamps, phosphor-coated LEDs, thin-film electroluminescent devices, phosphorescence OLEDs, inorganic/organic LEDs, LEDs using quantum dot technologies, LED arrays, flood light systems using LEDs, white LEDs, filament lamps, arc lamps, gas lamps and fluorescent tubes.

Dichroic beamsplitter 116 is used to both reflect and filter light, depending upon the direction the light is traveling toward dichroic beamsplitter 116. In one direction, dichroic beamsplitter 116 reflects blue light emitted by laser 100 to direct laser light 102 through an opening 81a in housing 81. In a second direction, dichroic beamsplitter 116 cuts blue light and allows green and red light to pass therethrough for reception by detector 90. Accordingly, dichroic beamsplitter 116 prevents any excitation light (in this case, blue light emitted by laser 100) from being received by detector 90. It should be appreciated that a combination of a reflective member (e.g., a dichroic mirror) and one or more light filters may be substituted for dichroic beamsplitter 116. In the embodiment illustrated in FIG. 1, filter 112 is preferably a dual band filter that permits only red and green light to pass therethrough and be received by detector 90.

As shown in FIG. 3, housing 81 includes a handle grip 84. A trigger 86 is provided to activate scanning unit 80, as will be explained below. A cable 82 electrically connects scanning unit 80 with control unit 40.

In the illustrated embodiment of the present invention, control unit 40 includes a display unit 42 (e.g., an LCD or LED display unit), a user input interface 44 (e.g., buttons, knobs, keypad, and the like) for control and programming of control unit 40, and an audio output 48 (e.g., a speaker) for emitting audible sounds. A power cord 50 connects control unit 40 to a power source (e.g., a conventional AC electrical outlet). The power source may also supply power to scanning unit 80 through control unit 40. Control unit 40 includes a processing unit and data storage to perform image processing on the light data collected by detector 90 and provides an audible and/or visual soil detection feedback using audio output 48 and display unit 42. A detailed description of the operation of control unit 40 and scanning unit 80 is provided below.

The present invention will now be further described with reference to detection of soil on articles that have been exposed to a solution containing a fluorescent agent (e.g., fluorescein, which is biocompatible). For example, a medical washer (washing apparatus) may be provided to remove bio-contaminants from articles placed in a washing chamber by directing jets or streams of fluid at the articles from spray heads or nozzles located within the washer chamber. The washer may be configured to expose the articles to a solution containing the fluorescent agent during the washer's standard wash cycle and/or rinse cycle. The fluorescent agent (non-specifically) binds to organic residues (e.g., proteins), and thus affixes to soil on the articles to label the bio-contaminant. Where there is no soil on the article, the fluorescent agent does not become affixed thereto (i.e., is unbound), and therefore can be easily rinsed off of the article. In a preferred embodiment, no extra wash time is required for labeling the bio-contaminant and no extra rinse time is required to remove all of the unbound fluorescent agent. Accordingly, no changes are required of existing medical washers with respect to standard wash and rinse cycles (i.e., no additional "marking" cycle, or pre-wash cycle, etc. is required). In one embodiment of the present invention, fluorescein is used as the fluorescent agent at a concentration in the range of about 0.001 mM to 90 mM (for example, around 0.3 mM) with an exposure time in the range of 30 seconds to 5 minutes to label the bio-contaminant.

It is contemplated that the washer may include a source of a fluorescent agent that is introduced into a water inlet line to the washing chamber during a desired stage of the washing and/or rinsing cycles. A valve controls the flow of the fluorescent agent into the water inlet line. Preferably, the solution containing the fluorescent agent is introduced into the washing chamber during a later stage of the washing cycle. Therefore, during a subsequent rinsing cycle, the fluorescent agent can be removed from unsoiled portions of the articles. The solution containing the fluorescent agent may be combined with a washing solution that includes a decontaminating agent or cleaning detergent. The decontaminating agent or cleaning detergent may initially be in a liquid or dry powder form. The fluorescent agent may be directly added to the decontamination or cleaning detergent before the detergent is added to the washing chamber.

It should be appreciated that while an illustrated embodiment of the present invention is described herein with reference to "fluorescein" as the fluorescent agent, it is contemplated that alternative fluorescent agents may be substituted for fluorescein. A selected fluorescent agent preferably has the following properties: approval by government regulatory authorities (e.g., FDA); bio-compatible in such a way that remaining traces of the fluorescent agent on an article can be safely introduced into the human body without incurring health problems; binds rapidly to proteins (e.g., within a few seconds); has the ability to withstand exposure to harsh washing environment conditions (i.e., harsh chemicals and temperatures exceeding 80° C.); water soluble; and high quantum yield. Alternative fluorophores include, but are not limited to, rose bengal, acid red, phtalocyanine, and luminol.

While the present invention has been described in connection with the use of a fluorescent agent, it is also contemplated that the present invention may be adapted for use with alternative chemical agents that provide luminescence, including but not limited to, chemical agents which provide phosphorescence, chemiluminescence, or bioluminescence.

Referring now to FIGS. 1 and 3, one or more articles 10 (e.g., a tool or instrument) which have been exposed to a solution containing fluorescein are placed in a tray 5. The articles are preferably arranged in a single layer to provide exposure to the light emitted by the light source, as will be described below.

An operator of soil detection system 30 grabs handle grip 84 to manually move scanning unit 80 over the surfaces of an article 10 while activating laser 100 using trigger switch 86. Activation of trigger switch 86 causes laser 100 to produce a laser light 102 at a wavelength of about 488-490 nm (blue light). The laser light 102 is reflected by dichroic beamsplitter 116 and travels through opening 81a of housing 81 and is directed toward article 10.

Figure 6A:
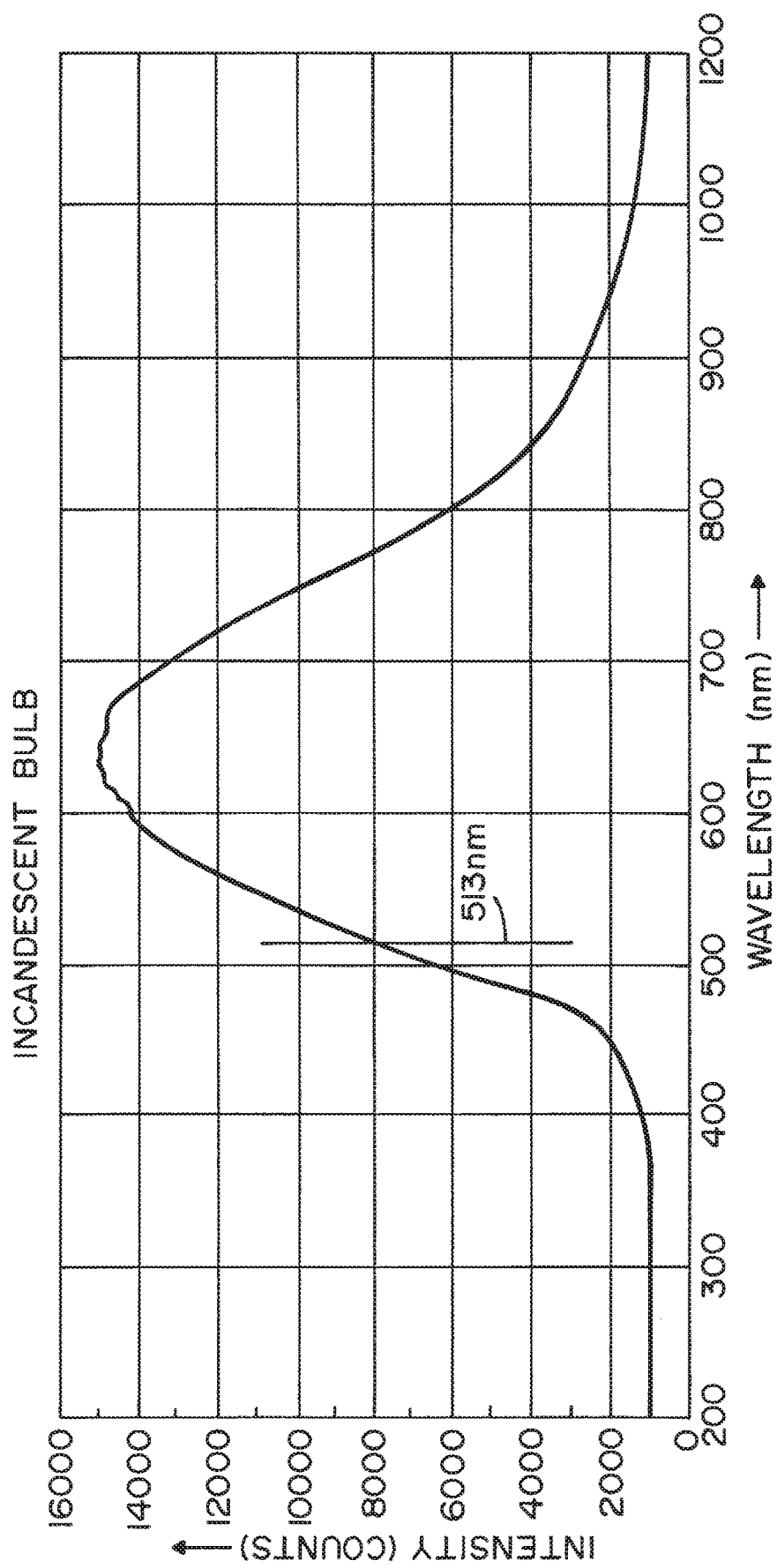
FIG. 6A is a graph illustrating the intensity of light emitted by an incandescent light bulb for a range of wavelengths.
Figure 6B:
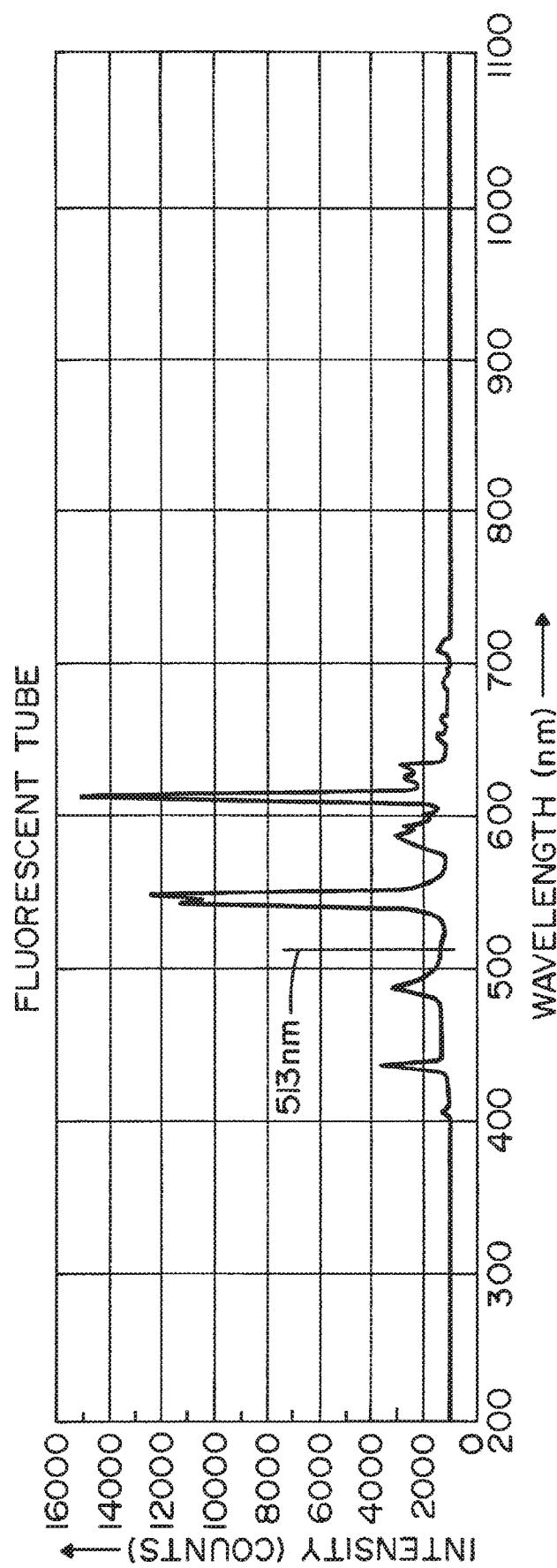
FIG. 6B is a graph illustrating the intensity of light emitted by a fluorescent light tube for a range of wavelengths.
Figure 6C:
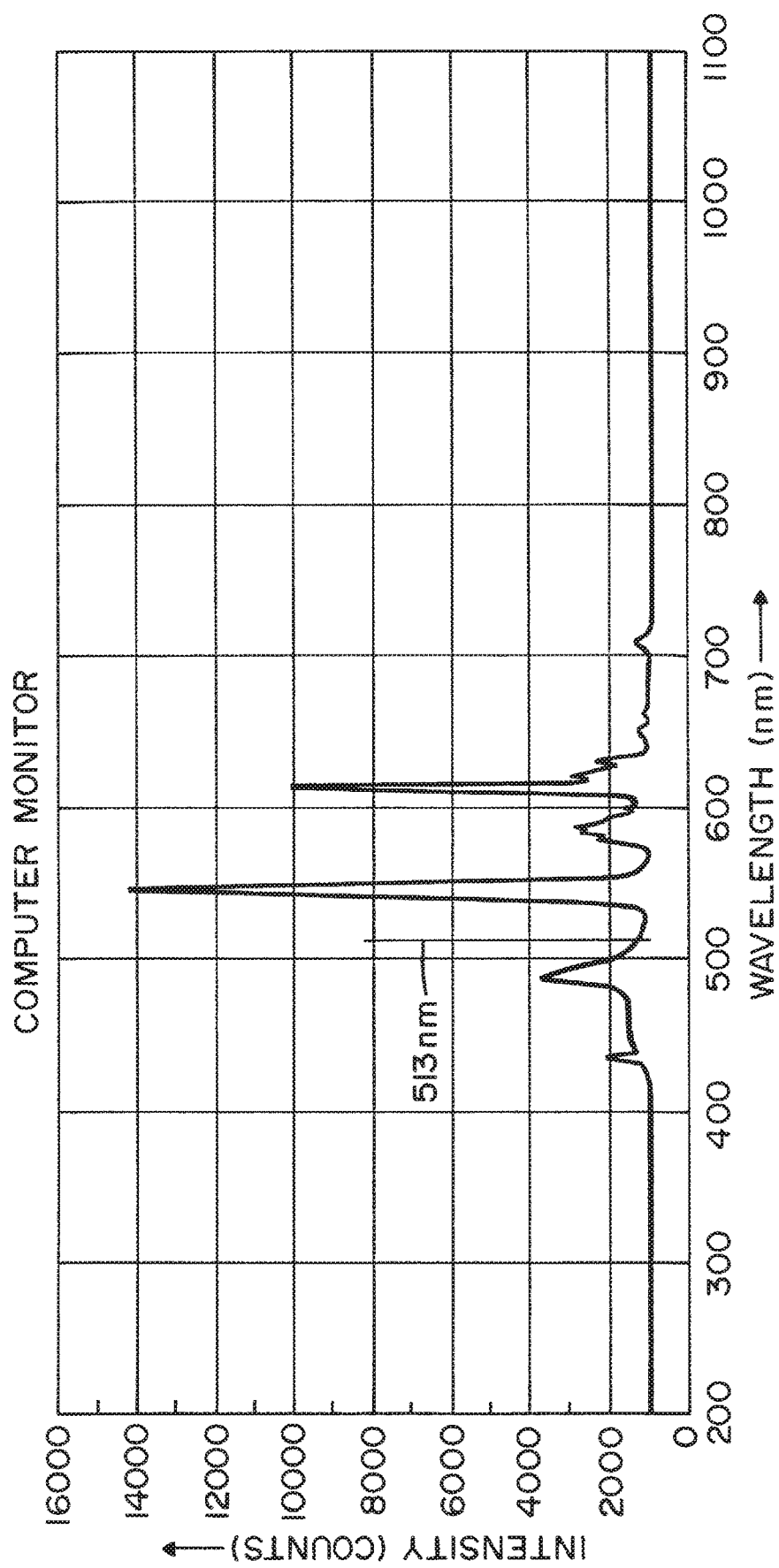
FIG. 6C is a graph illustrating the intensity of light emitted by a computer monitor for a range of wavelengths.

Article 10 is exposed to both ambient light and laser light 102 as scanning unit 80 is moved over the surfaces of article 10. FIGS. 6A-6C show the intensity of ambient light produced at various wavelengths for ambient lighting sources, such as an incandescent bulb, a fluorescent tube light, and a computer monitor screen, respectively. As discussed above, when the fluorescein that binds to soil is exposed to the laser light 102 at a wavelength of about 488-490 nm, the fluorescein emits light (i.e., fluoresces) at a wavelength of about 513 nm.

Reflected ambient light ($L_R$) and fluorescent light ($L_F$) emitted by the excited fluorescein pass through dichroic beamsplitter 116 and filter 112 before traveling through lens 94 of detector 90. Filter 112 allows only red and green light to pass therethrough to detector 90. The light transmitted through lens 94 is received by image sensor 92.

As scanning unit 80 is moved across article 10, the user squeezes trigger 86, thereby activating laser 100 to produce laser light 102 that is emitted from housing 81 through opening 81a. Laser light 102 is incident on article 10 as scanning unit is moved across article 10. Ambient light is also incident upon article 10, thereby producing ambient light reflections that will include both red and green light. When the fluorescent agent (i.e., fluorescein) present in the soil is excited by laser light 102 the soil fluoresces thereby emitting light at a wavelength of about 513 nm (green light). Both the reflected ambient light ($L_R$) and the fluorescent light ($L_F$) of the soil pass through filter 112 which filters out all but red and green light. Therefore, image sensor 92 only receives red and green light.

Referring now to FIG. 1, there is shown a sample input spectrum 120. As scanning unit 80 is moved across article 10, image sensor 92 acquires and transmits to control unit 40 detected light data indicative of input spectrum 120 that includes a green light waveform 122 and a red light waveform 124. Green light waveform 122 is indicative of the intensity of green light detected by image sensor 92 and red light waveform 124 is indicative of the intensity of red light detected by image sensor 92.

Control unit 40 is programmed to spectrally discriminate between soil fluorescence (indicating the presence of soil) and specular ambient light reflections, based upon the measure of saturation of green light intensities relative to red light intensities (ratio). In the illustrated embodiment, the range of this measure of saturation is enclosed between zero and one. Accordingly, the system is robust to the variations of ambient light of the surrounding environment and changes of acquisition parameters. A value of saturation close to zero is indicative of the presence of specular ambient light reflections, whereas a large value close to one is indicative of the presence of soil.

Control unit 40 may be programmed to display the detected light data to a user on display unit 42. Control unit 40 may also be programmed to provide the user with a visual and/or audible indicator (e.g., warning/alarm/feedback) via display unit 42 and audio output 48 in the event that the ratio of green light intensity-to-red light intensity indicates the presence of soil. It is further contemplated that control unit 40 may present an image of article 10 and use display unit 42 to display the location of the detected soil (i.e., contaminated region) on article 10. The image of article 10 may be acquired during optical scanning of article 10 or from a prestored image library comprised of images of a plurality of commonly used articles 10.

Figure 2:
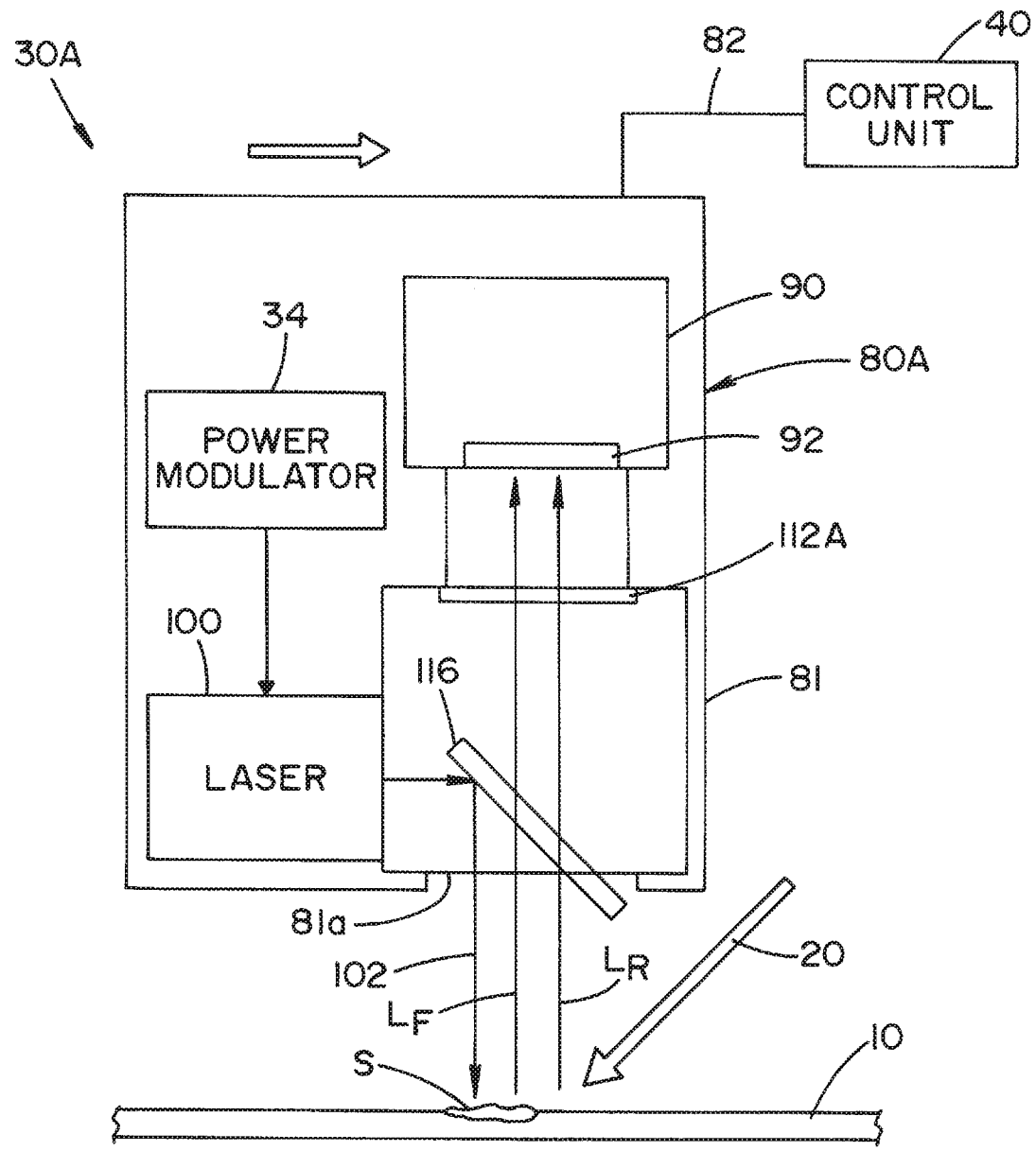
FIG. 2 is a schematic view of a soil detection system according to a second embodiment of the present invention.

Referring now to FIG. 2, there is shown a soil detection system 30A according to an alternative embodiment of the present invention. Soil detection system 30A is similar to soil detection system 30 in several regards, and thus like components have been given the same reference numbers. Soil detection system 30A includes scanning unit 80A having laser 100, detector 90, a power modulator 34, dichroic beamsplitter 116, and a light filter 112A that allows only green light to pass therethrough. Power modulator 34 produces a pulsed waveform that provides an ON/OFF signal to activate/deactivate laser 100. When the pulse is an ON signal, laser 100 is activated to produce laser light 102. The pulsed waveform causes laser 100 to be continuously pulsed ON and OFF at a laser modulation frequency. As scanning unit 80A is moved across article 10, the user squeezes trigger 86, thereby activating power modulator 34 to produce the pulsed waveform that provides the ON/OFF signal to laser 100. When the pulse is an ON signal, laser light 102 is emitted from housing 81 through opening 81a.

It should be appreciated that power modulator 34 may alternatively take the form of a square wave modulation circuit to modulate the output of laser 100 (amplitude modulation).

Laser light 102 is incident on article 10 as scanning unit is moved across article 10. Ambient light is also incident upon article 10, thereby producing ambient light reflections that will include green light. When the fluorescent agent (e.g., fluorescein) present in the soil is excited by laser light 102 the soil fluoresces thereby emitting light at a wavelength of about 513 nm (green light). Both the reflected ambient light ($L_R$) and the fluorescent light ($L_F$) of the soil pass through filter 112 which filters out all but green light. Therefore, image sensor 92 only receives green light. In this embodiment, image sensor 92 may take the form of a color or gray-scale type sensor.

The modulation frequency for laser 100 is set to be lower than the emission frequencies of ambient lighting sources. Detector 90 operates in a continuous (video) mode at a frame rate that is higher that the modulation frequency. Green blinking features on display unit 42 of control unit 40 at the modulation frequency are indicative of soil. Non-blinking features or blinking at frequencies other than the modulation frequency are identified as ambient light reflections. In one embodiment of the present invention the modulation frequency is around 10 Hz. The frequency of ambient lighting sources are f=20-60 kHz (electronic ballast fluorescent tube), f=120 Hz (incandescent light bulb and magnetic ballast fluorescent tube), and f=240 Hz (computer monitor).

As scanning unit 80A is moved across article 10, power modulator 34 produces the pulsed waveform that causes detector 90 and laser 100 to be continuously pulsed ON and OFF. As indicated above, filter 112A only allows green light to pass therethrough to detector 90. Image sensor 92 acquires and transmits to control unit 40 detected light data indicative of the intensity of green light detected by image sensor 92.

Figure 5:
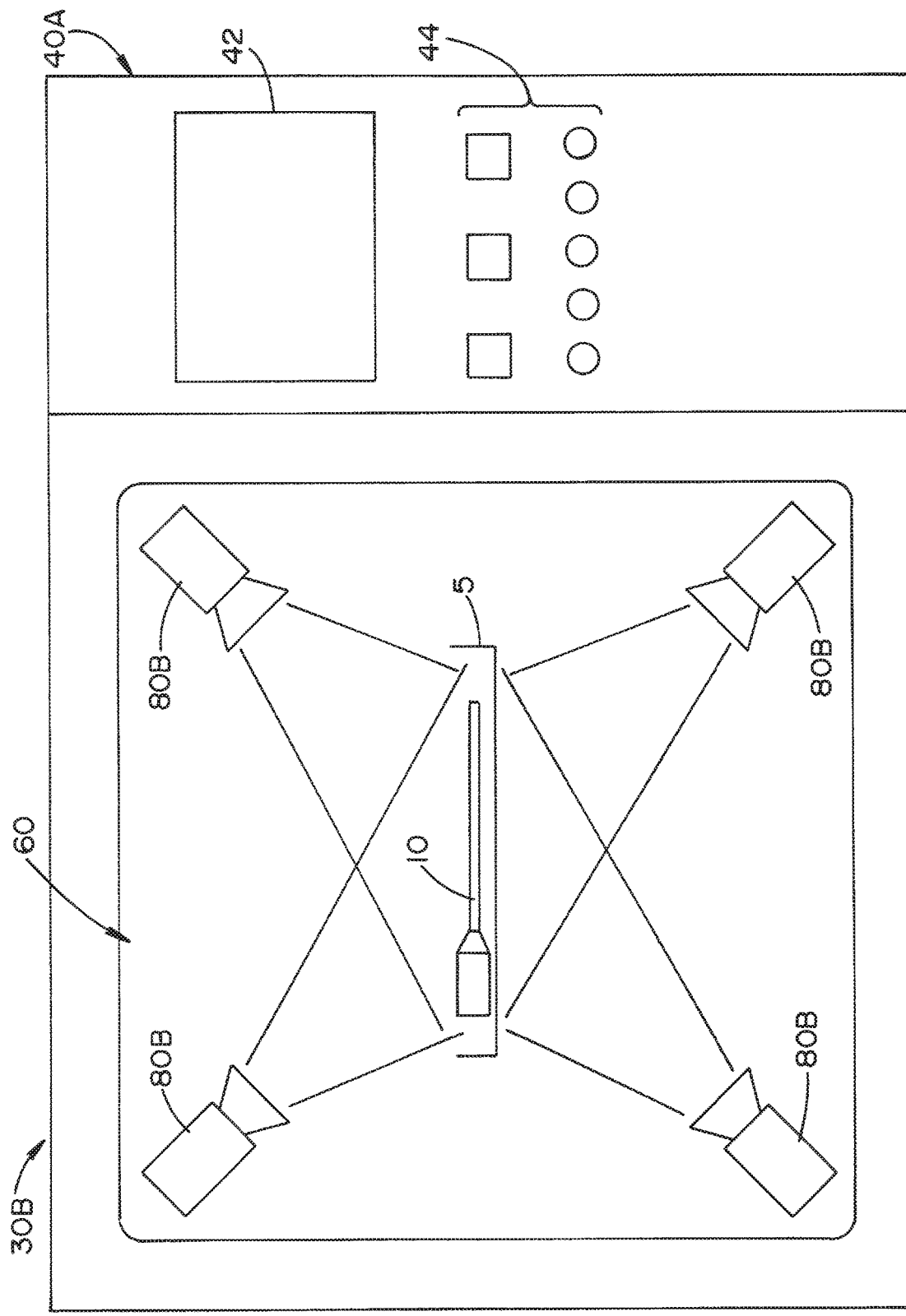
FIG. 5 illustrates a soil detection system according to an alternative embodiment of the present invention.

FIG. 5 illustrates a soil detection system 30B according to an alternative embodiment of the present invention. Soil detection system 30B includes a control unit 40A having an inspection chamber 60 for inspecting articles 10 placed on a tray 5. A plurality of scanning units 80B are located within chamber 60 for exposing the plurality of surfaces of an article 10 to laser light 102. Scanning units 80B are similar in most respects to scanning units 80 and 80A except that they are automatically activated by control unit 40A. The embodiment shown in FIG. 5 eliminates the need for the user to manually activate a handheld scanning unit 80, 80A and manually expose all of the surfaces of an article 10 to laser light 102.

It is contemplated that tray 5 may also be connected with an apparatus (now shown) for rotating, shaking, or otherwise moving tray 5 within chamber 60. It is further contemplated that scanning units 80B may be mounted to moveable arms (not shown) to provide a range of motion for each scanning unit 80B. Control unit 40 is programmed to control movement of tray 5 and scanning units 80B.

Figure 7:
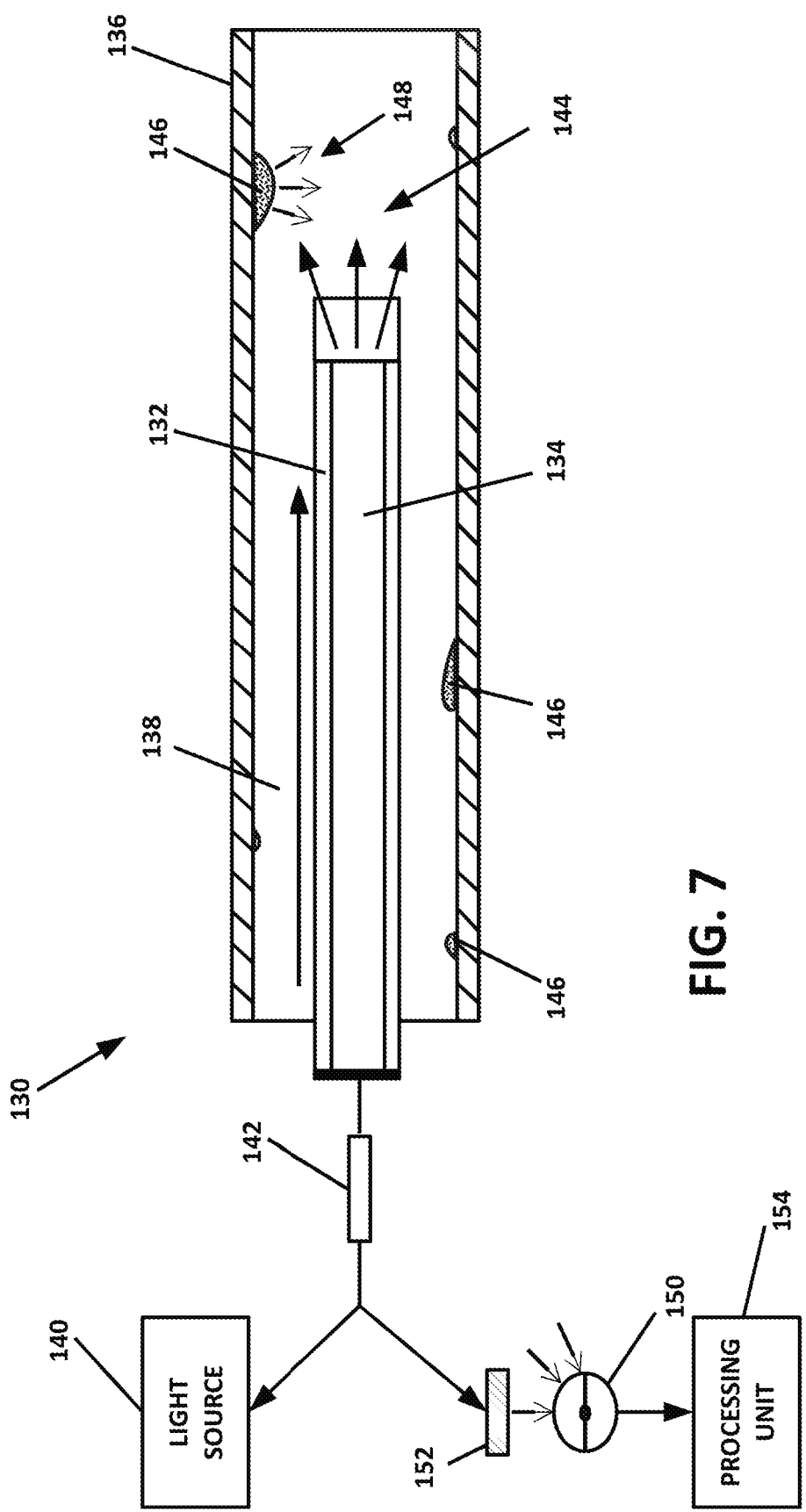
FIG. 7 illustrates a soil detection system for inspecting the interior of lumen of an endoscope according to an alternative embodiment of the present invention.

Referring now to FIGS. 7-10, there is shown a soil detection system and accompanying method according to an alternative embodiment of the present invention. FIG. 7 depicts a lumen inspection apparatus 130 including a probe 132 having an optical fiber 134. A distal end of the probe 132 is inserted into the interior of a cannulated structure such as a lumen 136.

As is understood in the art, an optical fiber 134 is formed of highly transparent glass, and possesses all the optical properties therewith. Optionally, the optical fiber 134 can be formed of a suitable polymer material such as poly (methyl methacrylate) (PMMA). This material can be used in an alternative embodiment of a disposable soil detection system. Light can be simultaneously transmitted outwardly and inwardly through the optical fiber 134, as occurs with a common, everyday window. Consequently, the present optical fiber 134 enables the simultaneous transmission of emitted excitation laser light and detected fluorescent light.

As with the other embodiments discussed in detail hereinabove, the lumen 136 was previously washed, prior to inspection, with a cleaning agent including fluorescein which binds to any residual soil that adheres to the interior of the lumen 136. The distal end of the probe 132 is inserted into the interior of the lumen 136 in an insertion direction 138 and at a constant insertion speed. As the probe 132 moves through the interior, emitted excitation light is transmitted through the optical fiber 134 from a light source 140 (e.g., a laser source). From the light source 140, the emitted excitation light is directed into the optical fiber 134 through a coupler 142, which provides an optical connection between the light source 140 and the optical fiber 134.

The emitted excitation light is emitted from the distal end of the probe 132 in an excitation pattern 144 which radiates in all directions within the interior of the lumen 136. The light of this excitation pattern 144 encounters any spots of residual soil 146 that adhere to any point along the interior of the lumen 136. The light from the excitation pattern 144 energizes the fluorescein that is bound on the soil 146. In response thereto, the fluorescein emits a fluorescence pattern 148 of fluorescent light at a different fluorescence wavelength which radiates in all directions.

At least a portion of the fluorescent light from the fluorescence pattern is received by the probe 132, and this fluorescence light is then transmitted through the optical fiber 134. In the preferred embodiment, as in other aforementioned embodiments discussed hereinabove, the excitation light from the light source 140 is laser light at a wavelength of about 488-490 nm, while the fluorescence wavelength is about 513 nm.

The fluorescent light travels back along the optical fiber 134 where it passes through the coupler 142. The coupler 142 is optically connected to a photodetector 150 and directs the received light toward the photodetector 150. A light filter 152 is disposed upstream of the photodetector 150, which passes only received light of the fluorescence wavelength and filters any excitation light which is also received at the distal end of the probe 132 from the interior of the lumen 136. The photodetector 150 converts the filtered fluorescent light into a corresponding electronic signal that can be further processed.

Figure 7B:
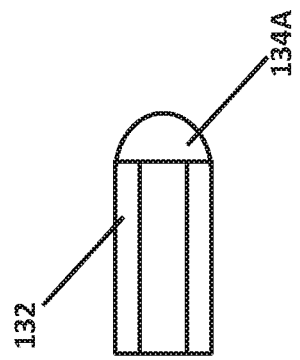
FIG. 7B illustrates a ball-shaped lens.
Figure 7A:
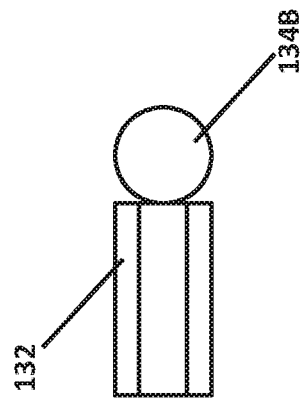
FIG. 7A illustrates a hemispheric lens.

The probe 132 can include an optical fiber 134 formed of glass or PMMA, as mentioned hereinabove. The fiber 134 can be a multimode fiber having a large core diameter of 100-1000 μm and a high numerical aperture (NA=0.2-0.5). Such a fiber 134 is preferably used to capture a maximum amount of fluorescent light. The fiber 134 is preferably cleaved at a 90 degree angle. The fiber 134 can optionally include a lens affixed at the tip for a larger exit cone angle of the excitation light pattern 144 shining inside the lumen 136. Such a lens also increases the capture cone angle of the fluorescence pattern 148 emitted in all directions from the soil 146. Such a lens can be a hemispheric lens 134A (FIG. 7A), a ball-shaped lens 134B (FIG. 7B), or of any other suitable custom design. The fiber probe 132 can be used as a disposable, one-time use device in order to avoid the need for cleaning in between inspections. Such disposability can be suitably implemented by using low-cost material such as plastic (e.g., PMMA) for the fiber 134 and the lens.

The photodetector 150 is electronically connected to a processing unit 154 for processing the signal of the fluorescent light received from the optical fiber as it is moved through the interior of the lumen 136. The processing unit 154 can be the control unit 40, as explained in detail hereinabove and as illustrated in FIG. 3. In this embodiment, the lumen inspection apparatus 130 can be electrically connected to the control unit 40 through a cable 82. The cable 82 can be configured to selectively attach the control unit 40 to the lumen inspection apparatus 130 or to the scanning unit 80, discussed in detail hereinabove. Alternatively, the processing unit 154 can be a standalone unit specifically dedicated to analyzing the received fluorescent light to determine the presence of soil 146 on the interior of the lumen 136.

Figure 8:
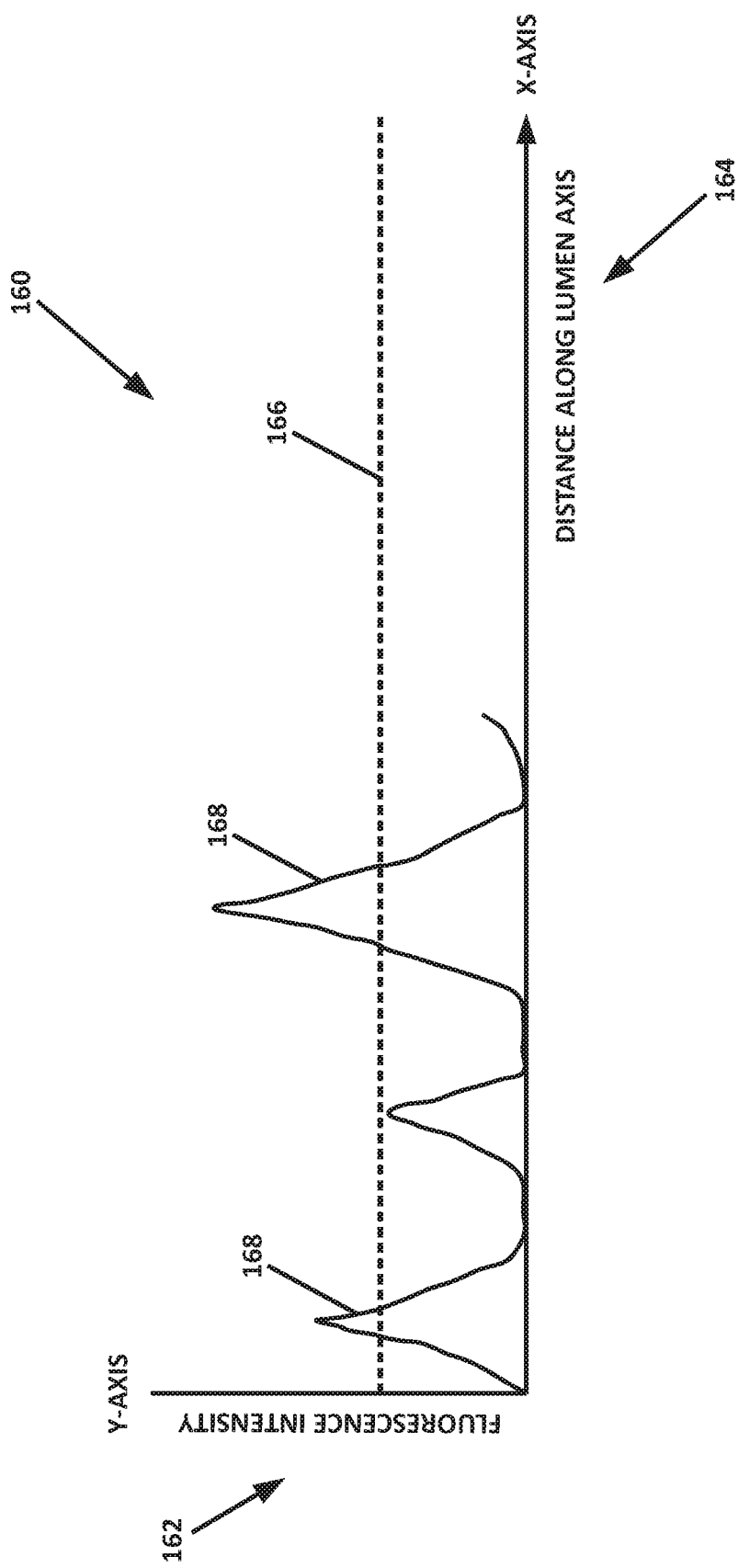
FIG. 8 is a graph illustrating a detected fluorescence intensity threshold indicative of the presence of soil at specific locations within the interior of a lumen of an endoscope.

FIG. 8 shows a graph 160 illustrating detected fluorescence intensity 162 with respect to distance 164 along a longitudinal axis of the lumen 136. As shown, the distance 164 is measured along the x-axis of the graph 160 and the intensity 162 is measured along the y-axis of the graph 160. A threshold 166 is indicated by the dotted line. This threshold 166 corresponds to a specific fluorescence intensity level indicative of the presence of an unacceptable level of residual soil.

The processing unit 154 detects instances of fluorescence intensity above the threshold in the light signal, which are registered as intensity spikes 168. Intensity spikes 168 that exceed the threshold 166 correspond to locations of an unacceptable level of residual soil within the interior of the lumen 136. These intensity spikes 168 are correlated with their respective distances along the longitudinal axis of the lumen 136 to determine the specific locations within the interior of the lumen 136 at which an unacceptable level of soil is present. It is to be appreciated that the intensity level indicated by the threshold 166 can be selectively adjusted to correspond with various cleanliness levels of residual soil, as may be desirable for various surgical and/or processing applications.

Figure 9:
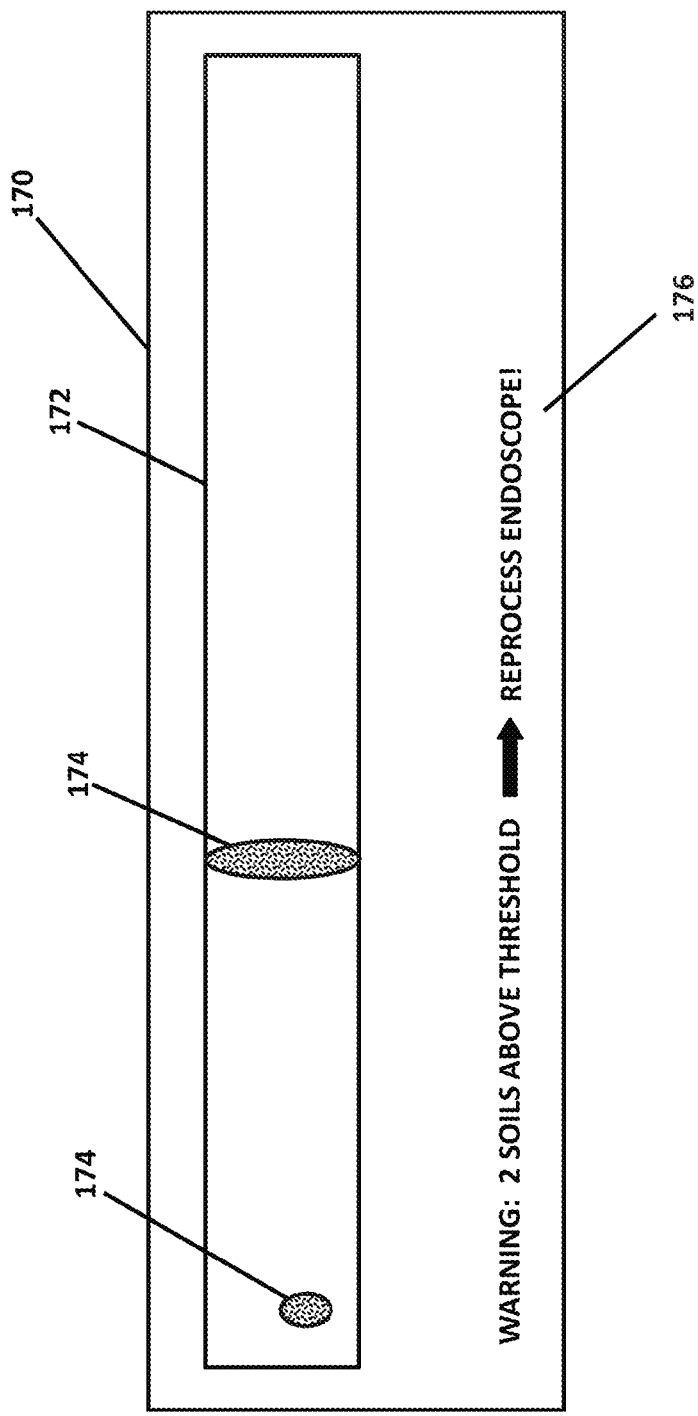
FIG. 9 depicts a user interface display indicating instances of unacceptable soil at specific locations within the interior of a lumen of an endoscope.

The results of the lumen inspection determined in the graph of FIG. 8 are presented to the operator in a user interface 170, as shown in FIG. 9. This user interface 170 includes a longitudinal display 172 corresponding to the length of the lumen 136. Spots 174 are shown at positions on the display 172 that correspond to the locations of the intensity spikes 168 within the interior of the lumen 136. The spots 174 can be sized to indicate the intensity level above the threshold 166 (i.e., a small spot 174 indicates an intensity only just above the threshold 166, corresponding to a small amount of residual soil, whereas a larger spot 174 indicates a higher intensity level above the threshold 166, corresponding to a larger amount of residual soil.)

The interface 170 can also include one or more alert messages 176 that indicate the status of the inspection process. As indicated in the figure, the interface 170 can indicate a specific number of spots 174 that indicate an unacceptable level of residual soil requiring reprocessing of the lumen 136. The interface 170 can alternatively indicate a collective size of all detected soil spots 174 having an aggregate area indicating an overall unacceptable soil level. The interface 170 can be incorporated into the control unit 40 or it can be a separate unit, detachably connected to the control unit 40 or used with a separate standalone unit specifically dedicated for the inspection of lumens 136.

Figure 10:
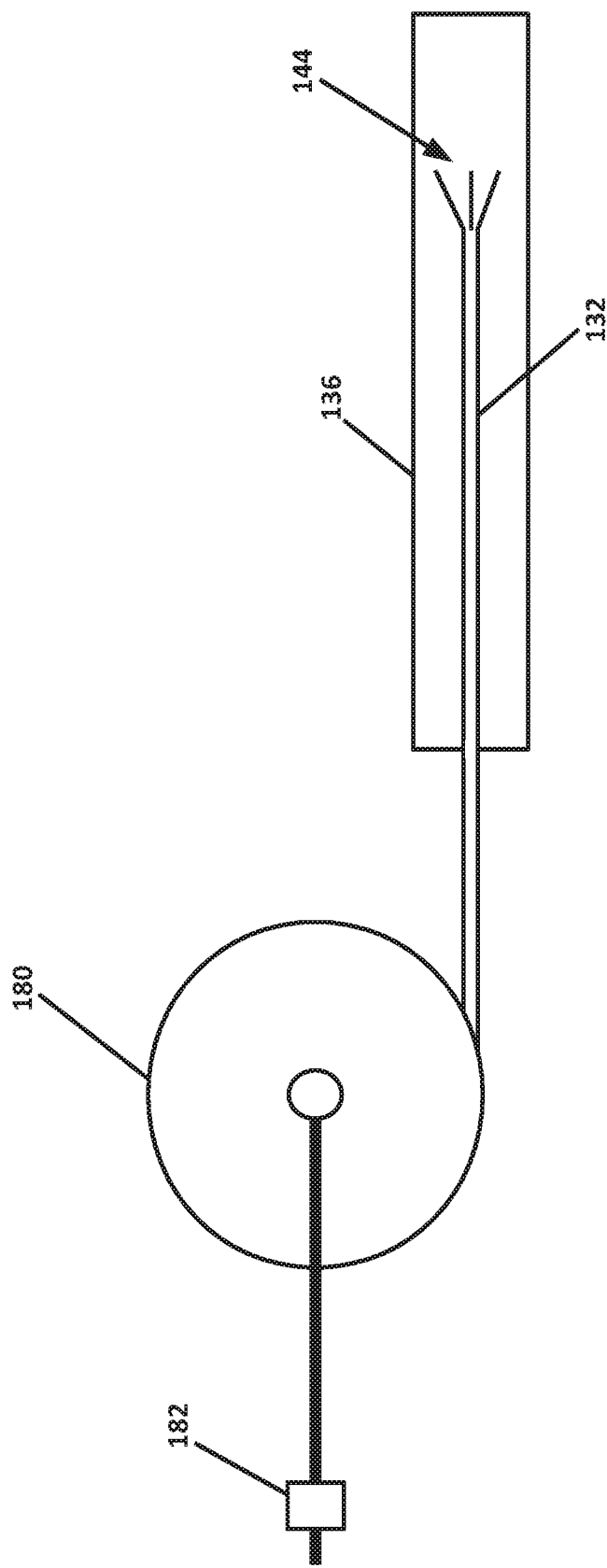
FIG. 10 illustrates a soil detection system for inspecting the interior of the lumen of an endoscope in conjunction with a probe reel for spooling and unspooling a probe.

FIG. 10 illustrates the soil detection system 130 used in conjunction with a probe reel 180 for spooling and unspooling the probe 132. The probe reel 180 can be similar to a standard-type take up reel used for various types of cable. In a "feed" mode, the probe reel 180 advances the distal end of the probe 132 into the interior of the lumen 136, whereupon the excitation pattern 144 is emitted and the inspection procedure is performed. In a "retract" mode, the probe reel 180 spools back the probe 132 at the completion of the inspection procedure.

The probe reel 180 can be motorized to enable power-driven feeding and retraction. In this embodiment, the feeding of the probe 132 can be specifically metered by the control unit 40, enabling the distal end of the probe 132 to be accurately controlled and positioned within the interior of the lumen 136. Alternatively, the probe reel 180 can be manually operated, using a handle or other device, as is common with similar structures such as fishing reels or garden hose assemblies. The probe reel 180 can include an input interface 182 for interfacing with the coupler 142 to enable optical connectivity to the light source 140 and the photodetector 150.

A proposed method is also disclosed that includes the steps of optically marking the soil on the interior surface of a lumen during a washing process, and thereafter, quantifying any soil remaining on the interior surface of the lumen after completion of the washing process.

In accordance with the proposed method, a fluorescent agent is introduced into a detergent or other cleaning agent during a wash cycle of a washing apparatus, wherein the fluorescent agent is bound to soil present within the interior of the lumen. Thereafter, the interior of the lumen is rinsed to remove unbound fluorescent agent. Next, the interior of the lumen is exposed to excitation light (i.e., laser light) by moving the distal end of the probe through the lumen in a longitudinal direction through the interior of the lumen. The fluorescent agent bound to residual soil is excited by the laser light, and thereby generates fluorescent light that is transmitted to the processing unit via the optical fiber.

The processing unit can provide a visual display of the detected intensity of the fluorescent light. The presence of soil is indicated by the detection of the fluorescent light, and the amount of residual soil is determined by the intensity level of the fluorescent light. Specific locations of residual soil are indicated on the visual display by intensity spikes. These intensity spikes are shown on the visual display at specific positions corresponding to the location of the residual soil within the interior of the lumen, along its longitudinal axis. The user can spool and unspool the probe using a structure similar to a standard-type take up reel used for various types of cable. In a "feed" mode, the distal end of the probe is advanced by the user into the interior of the lumen, whereupon the inspection procedure is performed. In a "retract" mode, the user spools back the probe at the completion of the inspection procedure.

The spooling and unspooling of the probe can be motorized to enable power-driven feeding and retraction by the user. This enables the feeding of the probe by the user to be specifically metered, enabling the distal end of the probe to be accurately controlled and positioned within the interior of the lumen. Alternatively, the probe can be manually fed and retracted by the user.

The foregoing description discloses specific embodiments of the present invention. It should be appreciated that these embodiment are described for purposes of illustration only, and that numerous alterations and modifications may be practiced by those skilled in the art without departing from the spirit and scope of the invention. For example, it is contemplated that the scanning unit of the present invention could communicate with the control unit via wireless communications. It is also contemplated that the method and apparatus of the present invention may also be used in combination with automated and human visual inspections using "white light" imaging. Further, as discussed above, it is further contemplated that the present invention may be adapted to include a fiber optic accessory for point inspection of cannulated instruments. It is intended that all such modifications and alterations be included insofar as they come within the scope of the invention as claimed or the equivalents thereof.

Having described the invention, the following is claimed:

1. A soil detection system for detecting presence of soil in a cannulated structure, the soil detection system comprising:
    a probe for insertion into an interior of the cannulated structure to detect a fluorescent agent bound to residual soil present on the interior of the cannulated structure, the fluorescent agent emitting fluorescent light at a fluorescence wavelength indicative of soil in response to excitation light at an excitation wavelength;
    a light source for producing the excitation light at the excitation wavelength, transmitted through a distal end of the probe into the interior of the cannulated structure;
    a light filter for filtering light emanating from the interior of the cannulated structure, said light emanating from said interior including the excitation light reflected by the interior at the excitation wavelength and the fluorescent light at the fluorescence wavelength emitted by exciting the fluorescent agent bound to the soil with the excitation light, said light filter configured to pass the fluorescent light indicative of soil;
    a photodetector for detecting the filtered fluorescent light emanating from said interior and generating a light signal corresponding thereto; and
    a processing unit for receiving the light signal generated by the detector to determine a presence of soil on the interior based upon features detected at the fluorescence wavelength within the interior of the cannulated structure,
    wherein the processing unit detects instances of fluorescence intensity above a threshold in the light signal, which correspond to locations of an unacceptable level of residual soil within the interior of the cannulated structure, and
    wherein the instances of fluorescence intensity above the threshold are correlated with their respective distances along a longitudinal axis of the cannulated structure to determine specific locations within the interior of the cannulated structure at which an unacceptable level of soil is present, and a longitudinal display corresponding to a length of the cannulated structure, for displaying locations within the cannulated structure where spots of residual soil are detected.

2. The soil detection system according to claim 1, wherein the cannulated structure comprises a lumen of a medical instrument.

3. The soil detection system according to claim 2, wherein the medical instrument is an endoscope.

4. The soil detection system according to claim 2, wherein the cannulated structure comprises pipes or tubes included in industrial equipment requiring inspection for organic residues.

5. The soil detection system according to claim 1, wherein the probe comprises an optical fiber that enables simultaneous transmission of the emitted excitation light and the detected filtered fluorescent light.

6. The soil detection system according to claim 5, wherein the optical fiber comprises a lens at a tip of the optical fiber.

7. The soil detection system according to claim 6, wherein the lens at the tip of the optical fiber is one of a hemispheric lens and a ball lens.

8. The soil detection system according to claim 1, wherein the fluorescent agent is fluorescein.

9. The soil detection system according to claim 1, further comprising a coupler for optically connecting the light source and the photodetector to the probe.

10. The soil detection system according to claim 1, wherein the excitation light from the light source is at a wavelength of about 488-490 nm, wherein the fluorescent light is at wavelength of about 513 nm.

11. The soil detection system according to claim 1, further comprising a user interface for displaying an output of the processing unit indicative of the presence of soil within the interior of the cannulated structure based upon features detected at the fluorescence wavelength.

12. The soil detection system according to claim 1, wherein an intensity level indicated by the threshold can be selectively adjusted to correspond with a predetermined cleanliness level.

13. The soil detection system according claim 1, wherein the longitudinal display includes at least one alert message for indicating a status of a cannulated structure inspection process.

14. The soil detection system according to claim 1, further comprising a probe reel for spooling and unspooling the probe.

15. The soil detection system according to claim 1, wherein the probe further comprises an image sensor for providing a view of the interior of the cannulated structure.

* * * * *